(12) United States Patent
Ogura et al.

(10) Patent No.: US 8,663,197 B2
(45) Date of Patent: Mar. 4, 2014

(54) FLEXIBLE CHANNEL FOR USE ON ENDOSCOPE

(75) Inventors: Akira Ogura, Tochigi (JP); Joji Watanabe, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 1265 days.

(21) Appl. No.: 11/806,497

(22) Filed: May 31, 2007

(65) Prior Publication Data

US 2007/0282304 A1  Dec. 6, 2007

(30) Foreign Application Priority Data

Jun. 2, 2006  (JP) ................................ 2006-154194

(51) Int. Cl.
*A61M 25/00* (2006.01)
*A61B 1/04* (2006.01)

(52) U.S. Cl.
USPC .......................................... 604/526; 600/128

(58) Field of Classification Search
USPC .......... 604/523, 526, 246; 600/139, 101, 140, 600/141, 144, 150, 128–130
See application file for complete search history.

(56) References Cited

U.S. PATENT DOCUMENTS

| | | | | | |
|---|---|---|---|---|---|
| 2,486,763 | A | * | 11/1949 | Roberts | 156/425 |
| 4,236,509 | A | * | 12/1980 | Takahashi et al. | 600/139 |
| 5,378,234 | A | * | 1/1995 | Hammerslag et al. | 604/95.04 |
| 6,899,674 | B2 | * | 5/2005 | Viebach et al. | 600/152 |
| 2003/0181785 | A1 | * | 9/2003 | Viebach et al. | 600/152 |
| 2004/0087885 | A1 | * | 5/2004 | Kawano et al. | 604/8 |

* cited by examiner

Primary Examiner — Bhisma Mehta
Assistant Examiner — Bradley Osinski
(74) Attorney, Agent, or Firm — Birch, Stewart, Kolasch & Birch, LLP

(57) ABSTRACT

A flexible channel to be incorporated into an endoscopic insertion portion having a flexible portion at least in part of its length, for the purpose of providing a flexible passage internally of the endoscopic insertion portion. The flexible channel is composed of a flexible tube with a helical groove on and around its outer periphery, and a reinforcing coil fitted in the helical groove on the flexible tube. At the root of the helical groove, angular projections are formed at intervals in the longitudinal direction and the reinforcing coil is tightly pressed tightly against the angular projections.

6 Claims, 7 Drawing Sheets

FLEXIBLE CHANNEL FOR USE ON ENDOSCOPE

This invention claims foreign priority to Japanese Patent Application No. 2006-154194 filed Jun. 2, 2006.

BACKGROUND OF THE INVENTION

1. Field of the Art

This invention relates to a flexible channel to be fitted in an endoscopic insertion portion to serve as a passage of forceps or other surgical or medical instruments, for insertion of operating wires or other components, or as a passage for sending a fluid into or out of a body cavity.

2. Prior Art

Generally, the so-called biopsy channel is provided in an endoscopic insertion portion for introduction of forceps or other treating instruments into a body cavity. The biopsy channel of this sort is extended forward from an manipulating head assembly as far as a fore distal end of an elongated insertion portion. In case the endoscopic insertion portion has a flexible section in part of its length, the biopsy channel needs to have a flexible structure in that section. Therefore, usually a biopsy channel is formed by the use of a flexible tube of a soft or pliable synthetic resin material and fitted in an endoscopic insertion portion in such a way that it is free from buckling when the insertion portion is bent or when it is pressed by other component parts which are fitted in the insertion portion. In order to retain the shape of the flexible tube, it has been a wide practice to wind a metal wire like a steel wire helically around the outer periphery of the flexible tube as a reinforcing coil. In this regard, normally a reinforcing metal wire is wound around a flexible tube in a predetermined pitch, usually in a wide pitch. In some cases, in order to hold helices of a reinforcing metal wire in predetermined position without increasing the diameter of the flexible tube, a helical groove is formed on the outer periphery of the flexible tube to anchor the reinforcing metal wire therein.

Shown in Japanese Laid-Open Patent Application H5-184533 is a method for forming a helical groove on the outer periphery of a flexible tube, which has thus far been in use in the art. In this prior art method, a blank flexible tube is set on a rotating means, and outer peripheral surface of the flexible tube is heated into a softened state while the flexible tube is rotated by the rotating means. In this state, a rotating die is pressed on the softened outer peripheral surface of the flexible tube and moved in the axial direction of the flexible tube to form a helical groove around the outer periphery of the flexible tube in a predetermined pitch. A reinforcing metal wire is then anchored in the helical groove to form a reinforced flexible channel.

An operator who grips an endoscopic insertion portion in his or her hand often tends to twist rod at the time of introducing the insertion portion into a body cavity or at the time of turning a distal end portion of the insertion portion into a different direction. When an endoscopic insertion portion is handled in that way, a biopsy channel which is fitted in the insertion portion is also subjected to a twisting force. A reinforcing coil in a helical groove around a flexible tube of the biopsy channel is not securely fixed in the groove, so that application of a twisting force may cause positional deviations to the reinforcing coil in the groove, leaving the coil in an instable state. In this connection, by the use of a reinforcing coil with an inside diameter which is smaller than a root diameter of the helical groove, the reinforcing coil can be pressed against root portions of the helical coil more tightly and anchored therein in a more stabilized state. However, since root portions of the helical groove on the flexible tube is very small in wall thickness, so that inward deformations may occur to these portions under the pressing force exerted by the reinforcing coil, forming inward protrusions on the inner periphery of the flexible tube to such a degree as to hinder insertion of forceps or other medical treating instruments.

SUMMARY OF THE INVENTION

In view of the foregoing situations, it is an object of the present invention to provide a flexible channel for use in an endoscopic insertion portion, the flexible channel having a shape-retaining reinforcing coil fitted in a very stabilized state within a helical groove on the outer periphery of a flexible tube, without forming protrusions or bumps on the inner periphery of the flexible tube to guarantee smooth passage of a medical treating instrument.

It is another object of the present invention to provide a flexible channel which is so arranged as to let a reinforcing coil in a helical groove on the outer periphery of a flexible tube positively bite on root portions of the helical groove and stay in position within the helical groove in a stabilized state free of positional deviations relative to the flexible tube.

It is still another object of the present invention to provide a method for manufacturing a flexible channel of the sort as mentioned above.

According to the present invention, in order to achieve the above-stated objectives, there is provided a flexible channel to be fitted into an endoscopic insertion portion having a flexible section at least in part thereof, for the purpose of forming a passage axially and internally of the insertion portion, the flexible channel comprising: a flexible tube having a helical groove on and around outer periphery thereof; and a reinforcing coil fitted in the helical groove on the flexible tube; the helical groove being provided with projections at intervals along a root portion thereof; and the reinforcing coil being tightly pressed against the projections at the root of the helical groove.

In this instance, at the root of the helical groove which is formed around a flexible tube, a large number of projections are formed successively during one revolution of a cutter wheel. The projections are not necessarily required to be so high but are preferred to have angular shapes or apexes. In this regard, it is most desirable for the root portion of the helical groove to have rough surface conditions, with a multitude of small projections in series in the longitudinal direction. In case ups and downs are formed at the root of the helical groove in this manner, the helical groove which is formed on and around the outer periphery of a flexible tube has a varying root diameter, including a maximum root diameter circumscribing the projections and a minimum root diameter circumscribing deepest points of the helical groove. Therefore, in the following description, a root diameter at the peaks of projections is referred to as "a maximum root diameter" while a root diameter at the deepest points of the groove is referred to as "a minimum root diameter."

The reinforcing coil should have an inside diameter smaller than the maximum root diameter of the helical groove. That is to say, the inside diameter of the reinforcing coil should not exceed the maximum root diameter of the helical groove. If the inside diameter of the reinforcing coil exceeds the maximum root diameter, it will become difficult for the coil to press root portions of the groove strong enough for maintaining positional stability. On the other hand, in case the inside diameter of the reinforcing coil is smaller than the minimum root diameter, obstructive protrusions and bumps may appear on the inner periphery of the flexible tube. Therefore, it is preferable that the inside diameter of the reinforcing coils be approximately equivalent to or slightly larger than the minimum root diameter and smaller than the maximum root diameter of the helical groove. By making arrangements in this way, it becomes possible to let the reinforcing coil bite firmly on root portions of the helical groove and stay in position in a stabilized state even when a twisting force is applied to the endoscopic biopsy channel.

Preferably, the reinforcing coil is formed of a spring metal wire, and wound in a relatively wide pitch rather than a tight and narrow pitch from the standpoint of securing suitable flexibility in bending directions and downsizing the outside diameter of the flexible channel. However, from the standpoint of shape retainability of the flexible channel, the pitch of the coil should not be widened to an excessive degree.

The reinforcing coil in the helical groove may protrude to a certain degree on the outer periphery of the flexible tube. However, for reducing the diameter of the flexible channel, it is preferred that the reinforcing coil be completely embedded in the helical groove without protruding on the outer side of the flexible tube. For this purpose, the wire diameter of the reinforcing coil should be approximately equivalent to or smaller than the depth of the helical groove at the peaks of the above-mentioned angular projections where the helical groove is shallowest. If desired, a thermally shrinkable sheathing tube may be fitted on the flexible tube, keeping the reinforcing coil securely in an embedded state by thermal shrinkage of the sheathing tube.

The above and other objects, features and advantages of the present invention will become apparent from the following particular description of the invention, taken in conjunction with the accompanying drawings which show by way of example some preferred embodiments of the invention. Needless to say, the present invention is not limited to particular forms shown in the drawings.

BRIEF DESCRIPTION OF THE DRAWINGS

In the accompanying drawings.

DESCRIPTION OF PREFERRED EMBODIMENTS

Figure 1:
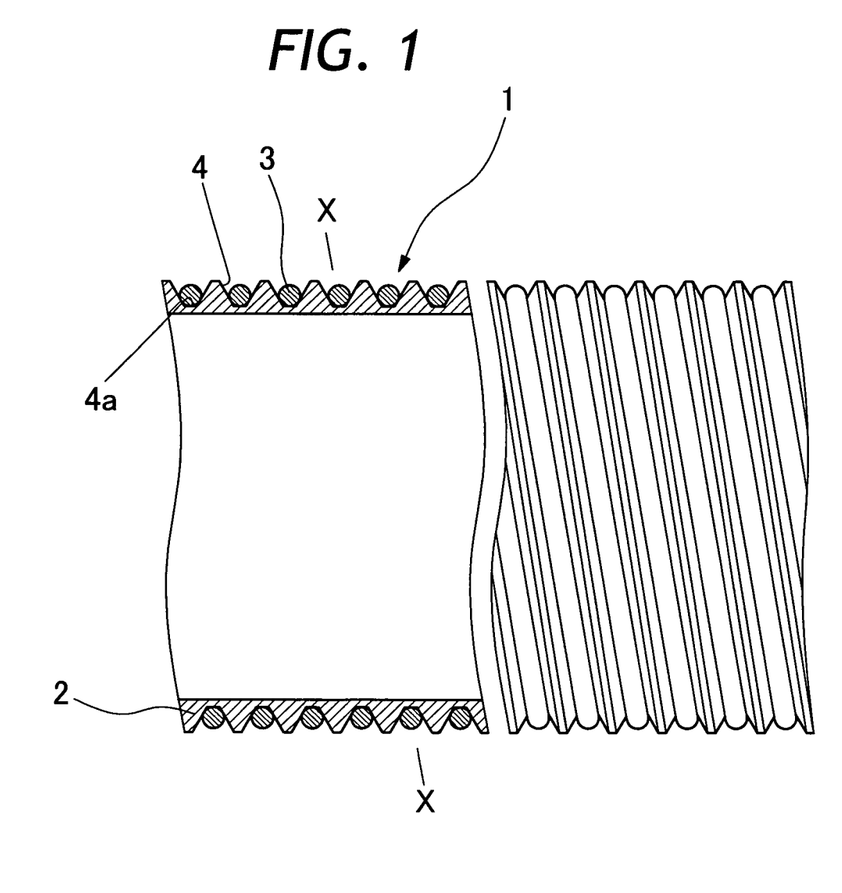
FIG. 1 is a fragmentary sectional view of a flexible channel embodying the present invention.

Hereafter, the present invention is described more particularly by way of its preferred embodiments. Shown in FIG. 1 is a fragmentary sectional view of a flexible channel according to the present invention. In this case, the flexible channel is extended from a manipulating head assembly to a fore distal end of an insertion portion of an endoscope to serve as the so-called biopsy channel for insertion of forceps or other medical treating instruments. However, it is to be understood that application of the flexible channel is not limited to a biopsy channel. For example, the flexible channel can be incorporated into an endoscopic insertion portion to provide a passage which is flexible in bending directions and which has satisfactory shape retainability, for example, to serve as a fluid supply passage or as a sheath of control cables.

As shown in the drawing, the flexible channel 1 is composed of a flexible tube 2 and a reinforcing coil 3. The flexible tube 2 is formed of a soft and pliable synthetic resin material. If necessary, a thin lining tube or coating of a material which has satisfactory properties in sliding contact and chemical resistance like a fluorine-base synthetic resin material is provided on interior surfaces of the flexible tube 2. A helical groove 4 is formed on and around the outer periphery of the flexible tube 2 in a predetermined pitch. The reinforcing coil 3 is embedded in the helical groove 4 to serve as a structural reinforcing member. The reinforcing coil 3 is formed of a spring metal wire and fitted in the helical groove 4.

That is to say, the reinforcing coil 3 is wound around the outer periphery of the flexible tube 2 in the same pitch as the helical groove 4 which is formed in a wide pitch in the axial direction of the flexible tube 2. The wire gage of the reinforcing coil 3 is smaller than the depth of the helical groove 4, so that the coil 3 is totally embedded in the helical groove 4 without projecting from the outer surface of the flexible tube 2. Thus, the flexible channel 1, having a coil of spring metal wire wound around the outer periphery of the flexible tube 2, is imparted with satisfactory shape retainability and anti-crush strength without impairing its flexibility in bending directions.

Figure 2:
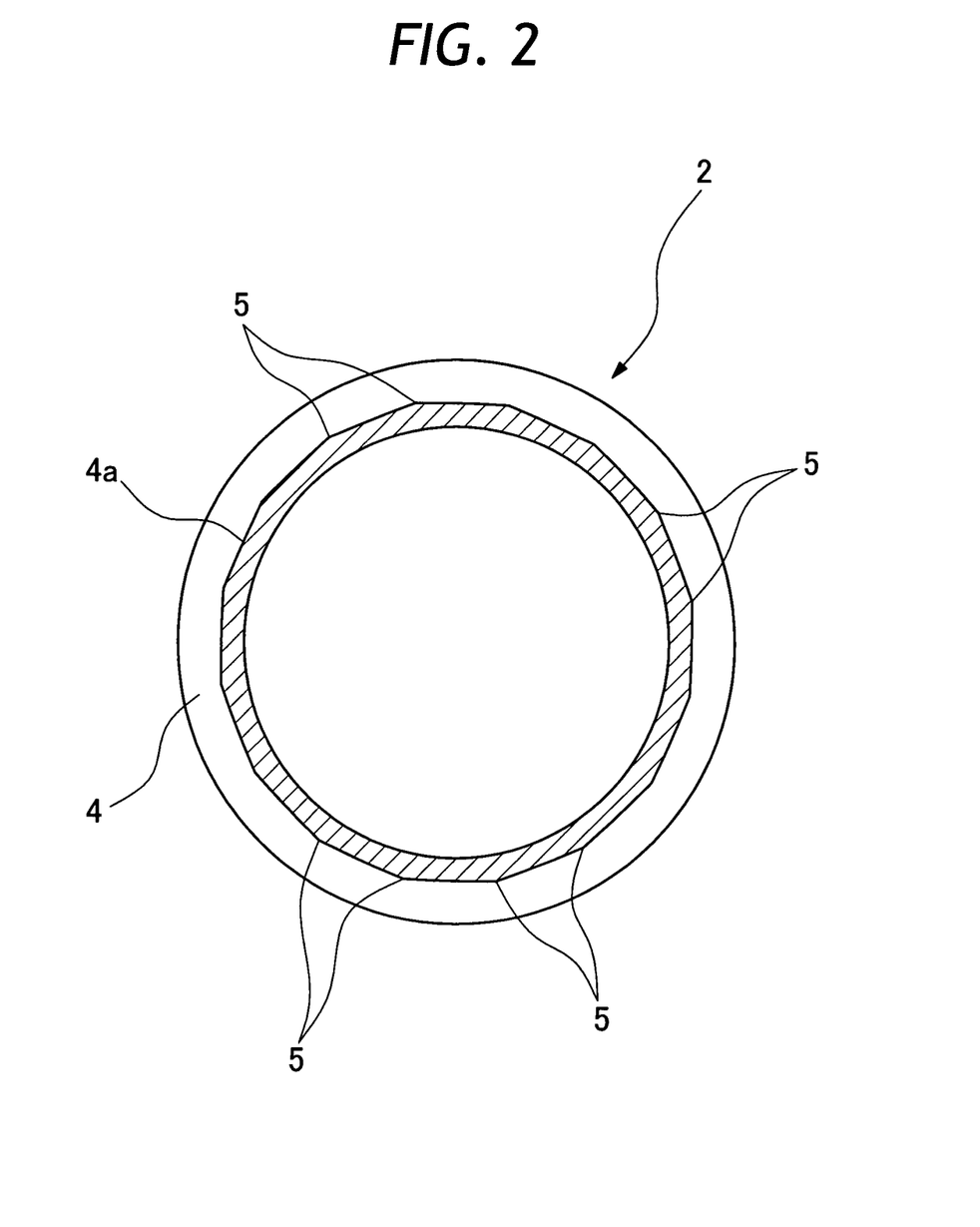
FIG. 2 is a schematic sectional view taken on line X-X of FIG. 1.

The reinforcing coil 3 which is fitted in the helical groove 4 on the flexible tube 2 should be retained there in a stable state, with almost no positional deviations even if a twisting force is applied to the flexible channel 1. For this purpose, as shown in FIG. 2, small angular projections 5 are formed at certain intervals along a root portion 4a of the helical groove 4. Namely, the root portion 4a of the helical groove 4 is not in a true circular shape, but is provided with small angular projections 5 at intervals in the longitudinal direction. The reinforcing coil 3 has an inside diameter approximately equivalent to a diameter of the flexible tube at deepest points at the root 4a of the helical groove (a minimum root diameter of the helical groove). Therefore, when the reinforcing coil 4 is fitted in the helical groove 4, it acts to push down the small angular projections 5. As a consequence, by relative rotations which take place between the coil 3 and the helical groove 4, the coil 3 is stably retained in the helical groove 4.

Figure 3:
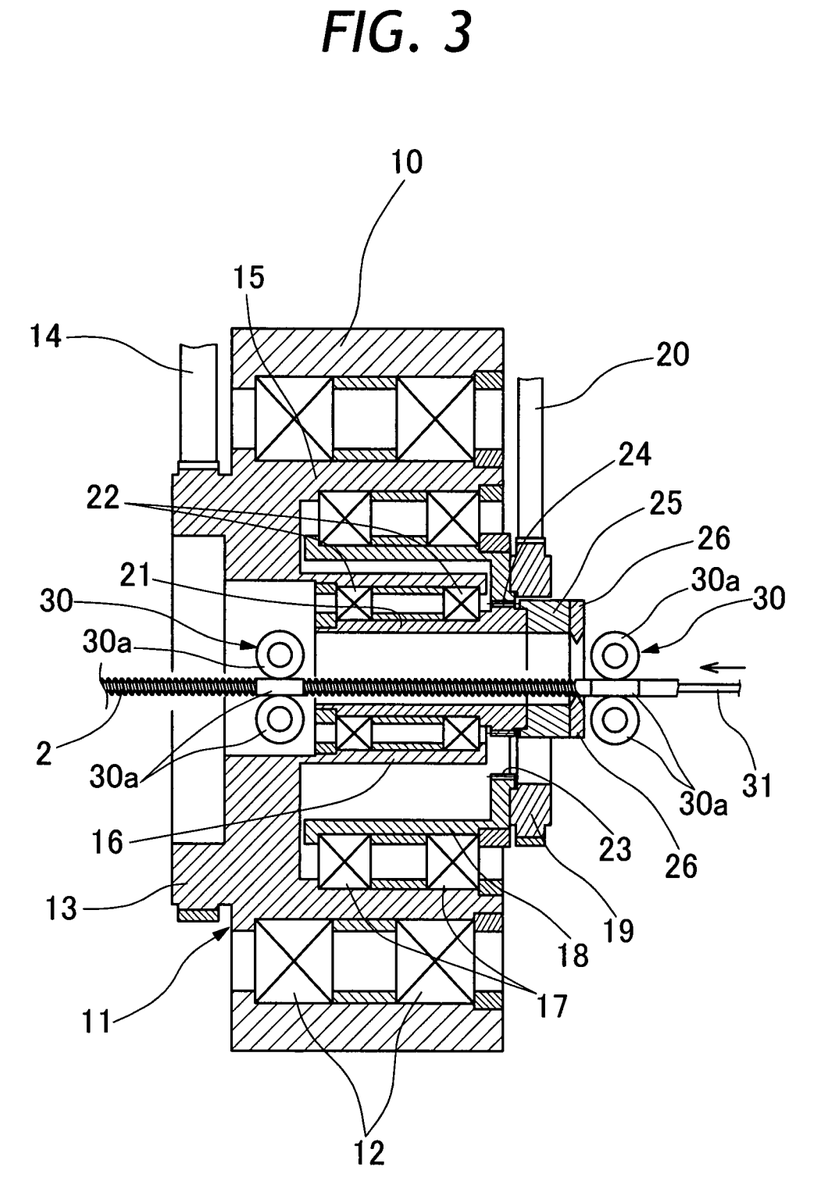
FIG. 3 is a sectional view of an exemplary groove cutter adopted for forming a helical groove around a flexible tube.
Figure 4:
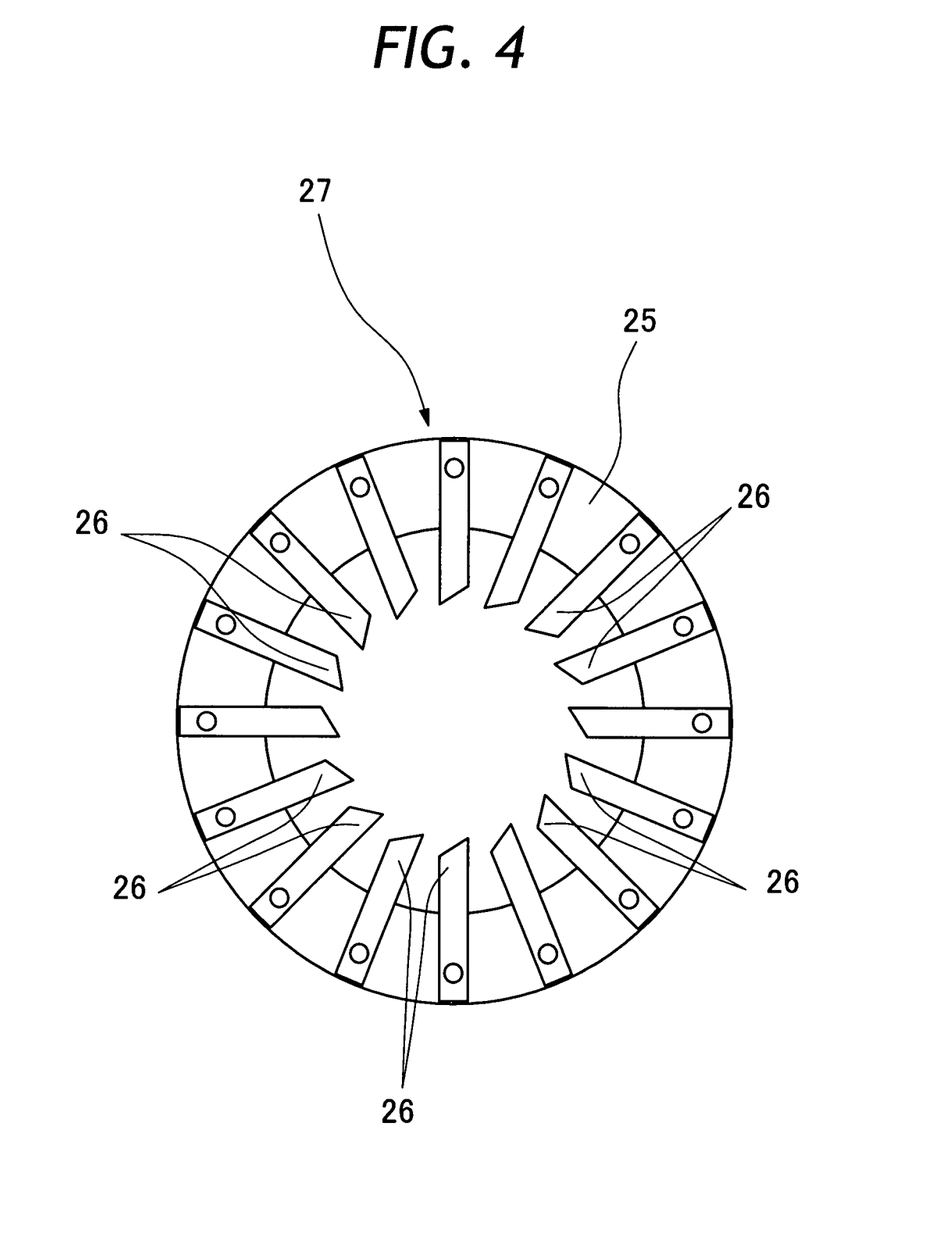
FIG. 4 is a front view of a cutter wheel for use on the groove cutter.
Figure 5:
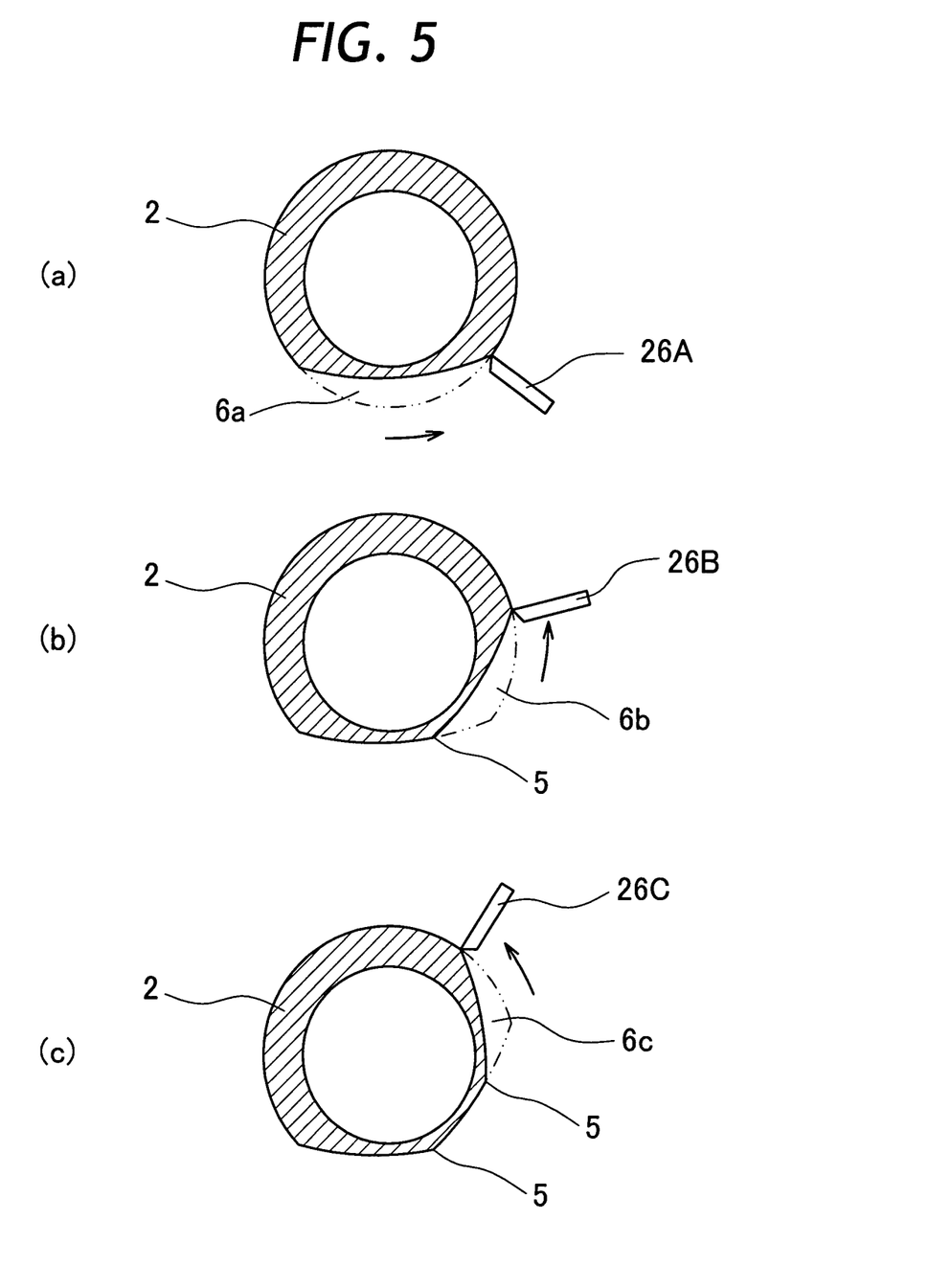
FIG. 5 is a schematic illustration showing steps of a grooving process for forming a helical groove around the flexible tube.

A helical groove 4, with small angular projections 5 along the root portion 4a as described above, can be formed on the outer periphery of the flexible tube 2, for example, by the use of a groove cutter as shown in FIGS. 3 to 5.

In FIG. 3, indicated at 10 is a holder ring of a groove cutter, which is fixedly set in a predetermined position. The holder ring 10 is tubular in shape, and a rotating drum 11 is rotatably supported internally of the holder ring 10 through bearings 12. A pulley 13 is mounted on the rotating drum 11, and a first drive belt 14 which is constituted by a timing belt, for example, is wrapped around the pulley 13 and a drive pulley, not shown, which is connected to a rotational drive means like an electric motor. Thus, by the first drive belt 14, the drum 11 is put in rotation. The rotating drum 11 is composed of a concentric rotating member 15 which is put in rotation concentrically relative to the holder ring 10, and an eccentric revolting member 16 which is mounted in an eccentric position relative to the concentric rotating member 15. It is the concentric rotating member 15 that is rotatably supported in the holder ring 10 through the bearings 12. The eccentric revolting member 16 is put in rotation in synchronism with the concentric rotating member 15, and at the same time revolved along an eccentric circular locus the diameter of which is determined by eccentricity of the revolving member 16 relative to the concentric rotating member 15.

A revolution drive drum 18 is rotatably supported internally of the concentric rotating member 15 of the drum 11 through bearings 17. For driving the revolution drive drum 18 into rotation, a second drive belt 20 is wrapped around a pulley 19 which is connected with the revolution drive drum 18. The revolution drive drum 18 is rotated in concentric relation with the rotating drum 11, to drive a rotating-revolving drum 21 which is put in dual rotating and revolving movements. In this instance, the rotating-revolving drum 21 is rotatably supported in the revolving member 16 through bearings 22.

A sun gear 23 which is formed on the inner periphery of the revolution drive drum 18 is meshed with a planet gear 24 formed on the rotating-revolting drum 21. Thus, the rotating-revolving drum 21 is put in a revolving movement relative to the revolution drive drum 18 by the revolving member 16 of the rotating drum 11, and at the same time it is rotated about its own axis as rotation of the revolution drive drum 18 is transmitted by way of the planet gear 24 which is meshed with the sun gear 23 on the revolution drive drum 18.

An annular cutter wheel 25 is attached to the rotating-revolving drum 21 which is simultaneously put in rotating and revolving movements. As shown in FIG. 4, for example, sixteen cutter blades 26 are attached on the cutter wheel 25 at predetermined angular intervals. The cutter blades 26 are extended radially inward to have respective cutting edges at inner distal ends which are successively brought to a cutting position for forming a helical groove 4 out of the outer periphery of the flexible tube 2. In this instance, the helical groove 4 is in V-shape in section, and the cutter blades 26 are shaped in conformity with the shape of the helical groove 4, more particularly, shaped in a linear form at a rotationally leading end and continuously increased in thickness toward a rotationally posterior end.

A blank flexible tube 2 is inserted into the rotating-revolving drum 21. At this time, the blank flexible tube 2 is located at the center of rotation of the rotating drum 11. Then, the blank flexible tube 2 is fed in the direction of an arrow in FIG. 3, supported by progressive feed means 30 which are located on the front and rear sides of the cutter wheel 25. A rod-like backing core 31 is placed in the flexible tube 2 to feed the soft flexible tube 2 in a stable state throughout a grooving operation free of twisting or bending or flattening or other deformations which may otherwise be caused by an externally applied pressure. In the case of the particular embodiment shown in FIG. 3, each unit of the progressive feed means 30 is composed of orthogonally located feed rollers 30a, which are put in rotation and pressed against circumferential surfaces of the flexible tube 2 to frictionally feed same progressively in a forward direction.

In this manner, the rotating-revolving drum 21 is rotated about its own axis and at the same time revolved eccentrically around the flexible 2 which is passed through the rotating-revolving drum 21 at a center position of the rotating drum 11. By these rotating and revolving movements of the drum 21, a plural number of cutter blades 26 which are set on the rotating-revolving drum 21 are successively driven across the flexible tube 2 to cut a helical groove 4 of a predetermined depth thereon while the flexible tube 2 is fed forward in the axial direction by the progressive feed means 30.

Shown in FIG. 5(a) is a phase of the grooving operation in which an outer peripheral portion of the flexible tube is cut off by a cutter blade 26, which is one of sixteen cutter blades 26 set on the cutter wheel 25. Since the cutter wheel 25 is mounted on the rotating-revolving drum 21 which is put simultaneously in a rotating movement on its own axis and a revolving movement about the flexible tube 2, the center of the rotating-revolving drum 21 is revolved in the direction of the arrow in FIG. 5(a) while the cutter holder 25 is rotated in the arrowed direction in the same figure. As a result, the cutter blade 26A is moved away from the flexible tube 2 as shown in FIG. 5(a) after cutting a segmental groove on the outer periphery of the flexible tube 2 with a predetermined inclination angle relative to the latter. At the same time, by a shift of the center axis of the rotating-revolving drum 21, a succeeding cutter blade 26B is brought to a cutting position and driven across the flexible tube 2 to cut a next segmental groove, which comes into communication with the first segmental groove formed by the cutter blade 26A at one point in the course of its cutting stroke. More particularly, the segmental groove formed by the cutter blade 26B is joined angularly with the preceding segmental groove of the cutter blade 26A at a point where the latter gets shallower to some extent past a deepest point. Further, as shown in FIG. 5(c), segmental grooves are cut successively by following cutter blades 26C, 26D, 26E and so on. During one revolution of the cutter wheel 25, segmental grooves are cut into the outer periphery of the flexible tube 2 continuously by all of the cutter blades 26, and the same cycle of cutting operation is repeated to form a helical groove on and around the outer periphery of the flexible tube 2.

Here, in order to form a helical groove 4 of a predetermined pitch continuously on and around the outer periphery of the flexible tube 2, it is necessary to adjust accurately the speed of rotation of the rotating-revolving drum 21, driven by the pulley 19, as well as the speed of revolution of the drum 21, driven by the pulley 13, in relation with the feed rate of the flexible tube 2 by the progressive feed means 30. In forming the helical groove 4, a segmental groove formed by one cutter blade is joined with a preceding segmental groove formed by a preceding cutter blade angularly at a point past a deepest point of the preceding segmental groove, forming a small angular projection 5 having an apex at the root 4a of the groove 4. Outer peripheral portions of the flexible tube 2 are cut off intermittently by the respective cutter blades 26. That is to say, outer peripheral portions of the flexible tube 2 are removed in the form of small and separate chips as indicated at 6a, 6b and 6c in FIGS. 5(a), 5(b) and 5(c), respectively, which are small and very unlikely to entangle around a component part of the groove cutter.

After forming a helical groove 4 on and around the outer periphery of a flexible tube 2 in the manner as described above, a reinforcing coil 3 of a metal wire is fitted into the helical groove 4 by a coil winding operation to obtain the flexible channel 1. The backing core 31 is retained in the flexible tube 2 throughout the grooving operation and until the end of the coil winding operation.

As mentioned hereinbefore, low angular projections are formed at intervals at the root 4a of the helical groove 4 by the grooving operation. That is to say, the wall thickness at the root 4a of the helical groove 4 is varied periodically in the radial direction, and there is a difference in distance from a center axis of the flexible tube 2 between a shallowest point at the peaks of the angular projection 5 and a deepest point of the helical groove 4 where the wall thickness of the flexible tube 2 is thinned down to a maximum degree. Therefore, the reinforcing coil 3 is so dimensioned as to have an inside diameter corresponding to the root diameter at the deepest point of the helical groove 4, namely, corresponding to the smallest root diameter of the helical groove 4. Therefore, when fitted in the helical groove 4, the reinforcing coil 3 acts to crush down the angular projections 5 at the root 4a of the helical groove 4, biting firmly on root portions of the helical groove 4 to remain in a predetermined position relative to the latter. Accordingly, in case the flexible channel 1 is incorporated into an endoscopic insertion portion to serve as a biopsy channel, the reinforcing coil 3 stays in position in an integrally assembled state, without undergoing positional deviations within the helical grooves 4 even when a twisting force is applied to the endoscopic insertion portion. Beside, the reinforcing coil 3 which is arranged to simply crush down the angular projections 5 at the root of the helical groove 4 does not give rise to surface irregularities or bumps on the inner peripheral side of the flexible tube 2. The inner peripheral surface of the flexible tube 2 remains free of surface irregularities to permit smooth insertion of medical treating instruments into and out of the biopsy channel.

Figure 6:
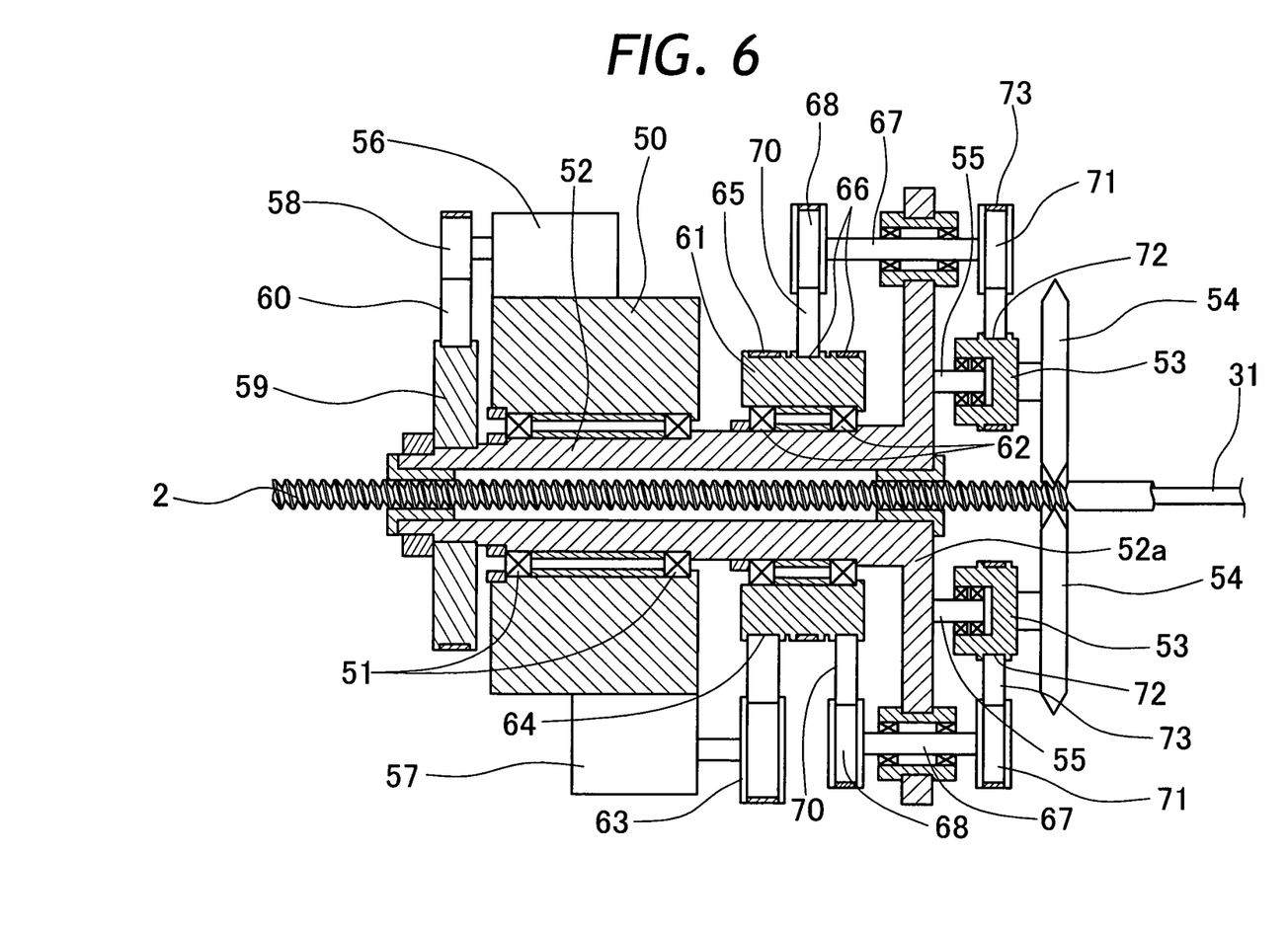
FIG. 6 is a sectional view of another exemplary groove cutter of a construction different from the one shown in FIG. 3.
Figure 7:
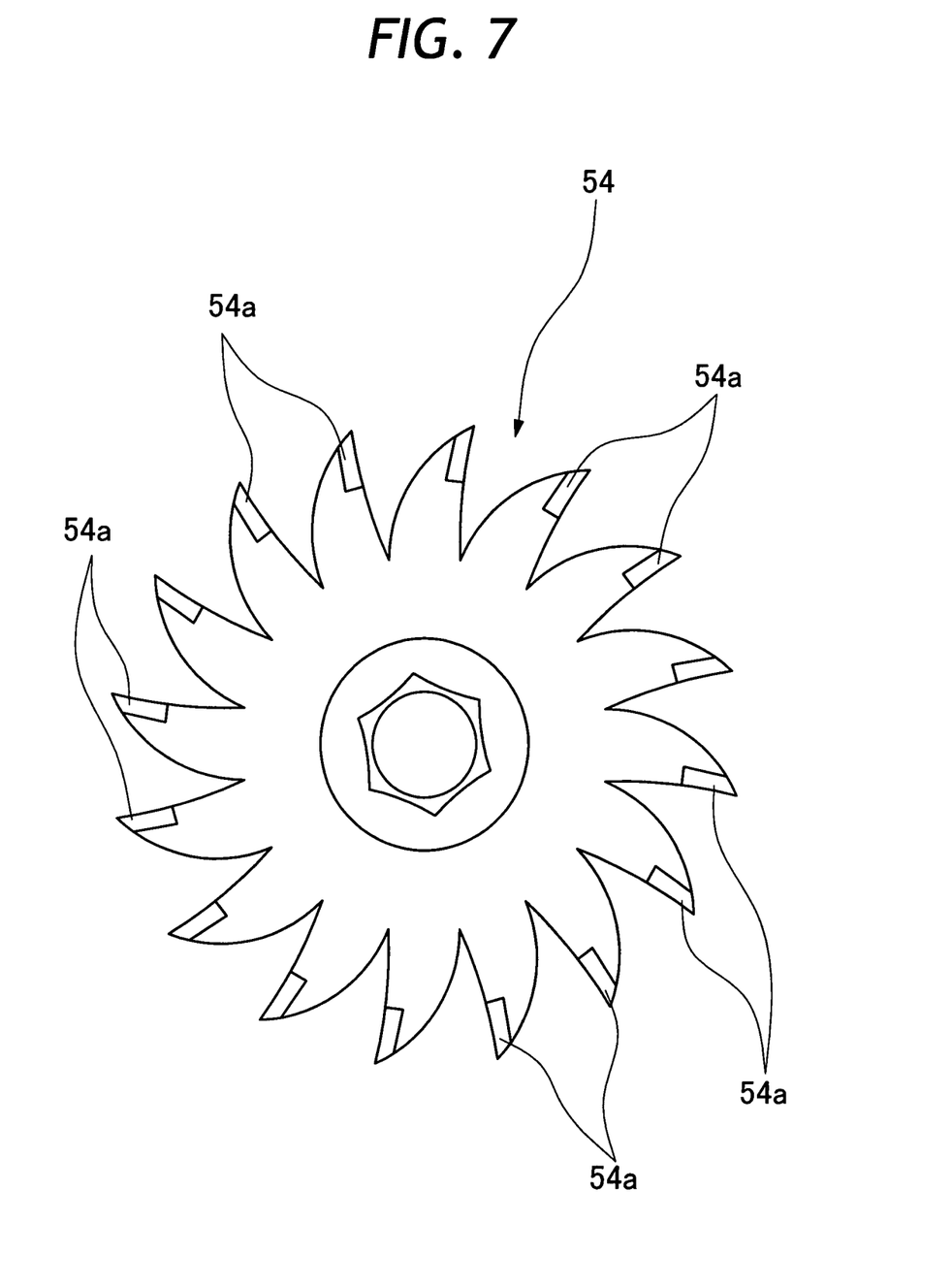
FIG. 7 is a front view of a cutter wheel for use on the groove cutter of FIG. 6.

In addition to the groove cutter shown in FIG. 3, a groove cutter of a different construction can be employed for the purpose of forming the helical groove 4 as long as it is capable of forming small angular projections 5 at intervals at the root 4a of the helical groove 4. A helical groove of this sort can also be formed on and around the outer periphery of the flexible tube 2 by the use of a groove cutter as shown in FIG. 6. In this case, a holder member 50 is set in position in concentric relation with a blank flexible tube 2 which is fitted on a backing core member 31, and a rotating drum 52 is supported in the holder member 50 through bearings 51. The rotating drum 52 is provided with a flange portion 52a at a front end thereof. A bearing member 53 is mounted on the flange portion 52a at a plural number of angularly spaced positions, for example, at two positions which are spaced from each other by 180 degrees. Supported in each bearing member 53 is a rotational shaft 55 of a cutter wheel 54 as shown in FIG. 7. The cutter wheel 54 is provided with a large number of radial cutter blades 54a which are arranged to cut segmental grooves successively on and around the outer periphery of the flexible tube 2.

Mounted on the holder member 50 are a revolving motor 56 and a rotating or spinning motor 57. A transmission belt 60 is wrapped around a pulley 58, which is mounted on the revolving motor 56, and a pulley 59 which is provided at the rear end of the rotating drum 52. A rotating ring 61 is rotatably mounted on the rotating drum 52 through bearings 62. A transmission belt 65 is wrapped around pulleys 63 and 64 which are mounted on the rotating motor 57 and the rotating ring 61, respectively. Driving transmission belts 70 are wrapped around a couple of pulleys 66, which are mounted on the rotating ring 61, and pulleys 68 on a couple of transmission shafts 67, which are rotatably supported on the flange portion 52a of the rotating drum 52 for rotation about the respective axes. Each one of the pulleys 71 which are mounted at the other axial ends of the transmission shafts 67 is coupled with a pulley 72 on an opposing bearing member 53 by a follower transmission belt 73.

By arranging the groove cutter in the manner as described above, the rotating drum 52 as a whole is put in rotation about the axis of the flexible tube 2 upon starting the revolving motor 56. At the same time, the two cutter wheels 54 are simultaneously put in rotation about the respective axes through the transmission shafts 67 upon starting the rotating motor 57. As a result, segmental grooves are successively and continuously cut in the flexible tube 2 to form a helical groove 4 around the outer periphery of the latter. Besides, since each one of the cutter wheels 54 is provided with radial cutter blades with cutting edges 54a located intermittently at predetermined angular intervals to form angular projections periodically at the root of a helical groove 4.

What is claimed is:

1. A flexible channel to be fitted into an endoscopic insertion portion having a flexible section at least in part thereof, for forming a passage axially and internally of said insertion portion, said flexible channel comprising:
    a flexible tube having a helical groove with a predetermined depth and around outer periphery thereof; and
    a reinforcing coil fitted in said helical groove on said flexible tube;
    projections intermittently formed on a root portion of said helical groove so as to have uneven surface with a plural number of apexes for the root portion of said helical groove; and
    said reinforcing coil being tightly pressed against said projections at the root of said helical groove such that said coil pushes down said apexes.

2. A flexible channel as defined in claim 1, wherein said reinforcing coil is formed of a metal wire coil wound in a relatively wide pitch.

3. A flexible channel as defined in claim 1, wherein said reinforcing coil is dimensioned to have an inside diameter equivalent to or larger than a minimum root diameter of said helical groove at deepest portions thereof but smaller than a maximum root diameter at said angular projections.

4. A flexible channel as defined in claim 1, wherein said helical groove has a depth larger than a wire diameter of said reinforcing coil at said projections, thereby completely embedding said reinforcing coil in said helical groove without permitting same to protrude on the outer periphery of said flexible tube.

5. A flexible channel as defined in claim 1, wherein surfaces at the root of said helical groove are roughened surfaces having a multitude of minute projections.

6. A flexible channel as defined in claim 1, wherein said flexible tube with said reinforcing coil is a biopsy channel of the endoscopic insertion portion.

* * * * *